(12) United States Patent
Hayden (10) Patent No.: US 11,426,131 B2
(45) Date of Patent: Aug. 30, 2022

(54) AUTOMATED MOTION CORRECTION IN PET IMAGING

(71) Applicant: Siemens Medical Solutions USA, Inc., Malvern, PA (US)

(72) Inventor: Charles Hayden, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 926 days.

(21) Appl. No.: 16/222,056

(22) Filed: Dec. 17, 2018

(65) Prior Publication Data
US 2020/0187874 A1    Jun. 18, 2020

(51) Int. Cl.
*A61B 6/03* (2006.01)
*A61B 6/00* (2006.01)
*G01R 33/48* (2006.01)
*G06T 11/00* (2006.01)

(52) U.S. Cl.
CPC ............. *A61B 6/037* (2013.01); *A61B 6/527* (2013.01); *G01R 33/481* (2013.01); *G06T 11/005* (2013.01); *G06T 2207/10104* (2013.01); *G06T 2207/30004* (2013.01)

(58) Field of Classification Search
CPC ......... A61B 5/055; A61B 6/032; A61B 6/037; A61B 17/00491; A61B 6/527; G06T 11/006; G06T 11/005; G06T 2207/10104; G01R 33/481
See application file for complete search history.

(56) References Cited

U.S. PATENT DOCUMENTS

| 7,421,101 B2* | 9/2008 | Georgescu ............ G06T 7/0016 382/128 |
| 8,073,109 B2 | 12/2011 | Gagnon et al. |
| 8,699,771 B2* | 4/2014 | Wollenweber ............ G06T 7/20 382/131 |

(Continued)

FOREIGN PATENT DOCUMENTS

RU    2008117160 A    11/2009

OTHER PUBLICATIONS

Jin, X., et al. "List-mode Reconstruction for the Biograph mCT with Physics Modeling and Event-by-Event Motion Correction" Phys. Med. Biol., Aug. 21, 2013, 58(16), pp. 1-33.

(Continued)

*Primary Examiner* — Baisakhi Roy (57) ABSTRACT

Methods and systems for automated motion correction of nuclear images are disclosed. A method includes receiving a first set of imaging data including a plurality if annihilation events detected during an imaging period and generating a plurality of four-dimensional volumetric images from the imaging data for the imaging period. Each four-dimensional volumetric image includes a target tissue. At least one motion correction is determined for each of the plurality of four-dimensional volumetric images. The at least one motion correction is determined using target tracking data generated for the target tissue over a time period associated with the four-dimensional volumetric image. Corrected image data is generated from the first set of imaging data and the at least one motion correction and at least one static reconstruction image including the target tissue during the imaging period is generated from the corrected image data.

17 Claims, 11 Drawing Sheets

(56) References Cited

U.S. PATENT DOCUMENTS

| | | | | |
|---|---|---|---|---|
| 8,805,037 | B2* | 8/2014 | Pack | G06T 11/006 |
| | | | | 382/128 |
| 9,730,664 | B2* | 8/2017 | Bal | A61B 6/037 |
| 2008/0298540 | A1* | 12/2008 | Serban | A61N 5/1048 |
| | | | | 378/18 |
| 2009/0281566 | A1* | 11/2009 | Edwards | A61B 5/062 |
| | | | | 606/214 |
| 2013/0303898 | A1* | 11/2013 | Kinahan | A61B 6/032 |
| | | | | 600/407 |
| 2015/0230762 | A1* | 8/2015 | Alpert | A61B 6/508 |
| | | | | 600/425 |
| 2016/0217596 | A1* | 7/2016 | Koehler | G06T 11/006 |
| 2016/0324500 | A1* | 11/2016 | Fan | G01R 33/5676 |
| 2019/0038239 | A1* | 2/2019 | Flohr | A61B 8/5223 |
| 2019/0261956 | A1* | 8/2019 | Srinivasan | G06V 10/20 |

OTHER PUBLICATIONS

Memmott, M. J., et al. "Impact of pharmacological stress agent on patient motion during rubidium-82 myocardial perfusion PET/CT." Journal of nuclear cardiology: official publication of the American Society of Nuclear Cardiology (2017).

Hunter, Chad R. R. N. et al., "Patient motion effects on the quantification of regional myocardial blood flow with dynamic PET imaging" Medical Physics, vol. 43, Issue 4, Apr. 2016, pp. 1829-1840.

Vleeming, E., et al. "Cardiac displacement during 13N-Ammonia myocardial perfusion PET/CT: comparison between adenosine and regadenoson induced stress." J. Nucl. Med. Technol 2018; 46:1-9 DOI: 10 2967/jnmt.117.199463.

Thompson, Andrea D. et al., "Rescued diagnostic quality by motion correction of dynamic cardiac positron emission tomography (PET) perfusion images" J. Nucl. Cardiol. Jan. 22, 2018, pp. 1-3 (doi:10.1007/s12350-018-1185-z).

Jizhe Wang et al: "Improved spatial and temporal resolution of gated myocardial perfusion PET using post reconstruction dual respiratory and cardiac motion compensation", 2014 IEEE Nuclear Science Symposium and Medical Imaging Conference (NSS/MIC), IEEE, Nov. 8, 2014 (Nov. 8, 2014), pp. 1-4.

Tao Feng et al: "Dual respiratory and cardiac motion estimation in PET imaging: Methods design and quantitative evaluation", Medical Physics., vol. 45, No. 4, Mar. 6, 2018.

Silin Ren et al: "Data-driven respiratory motion estimation and correction using TOF PET list-mode centroid of distribution", 2014 IEEE Nuclear Science Symposium and Medical Imaging Conference (NSS/MIC), IEEE, Nov. 8, 2014 (Nov. 8, 2014), pp. 1-5.

International Search Report for Corresponding International Patent Application No. PCT/US2019/043855, dated Oct. 23, 2019.

* cited by examiner

AUTOMATED MOTION CORRECTION IN PET IMAGING

FIELD

Aspects of the present disclosure relate in general to nuclear imaging systems, and more particularly to motion correction for nuclear imaging systems.

BACKGROUND

Time-of-flight (TOF) nuclear imaging, such as TOF positron emission tomography (PET), is used to construct two-dimensional and/or three-dimensional images of structures within a patient. TOF PET (and other TOF nuclear imaging) detects coincidence events representing near simultaneous detection of annihilation photon pairs using a pair of detectors. The TOF PET system determines the difference in time between the detection of the two photons (e.g., the time of flight) and localizes the point of origin of the annihilation event that occurred between the two detectors.

PET imaging of individual organs can include at-rest scans and/or stress scans of the target organ. During both at-rest and stress scanning, periodic and non-periodic motion of the organ can result in image blur or defects. Periodic motion includes recurring, expected motion of the organ, such as a heart-beat, respiratory motion, etc. Non-periodic motion, which often occurs during stress cans, includes unexpected or sudden and/or non-repeating motion, such as movement of a patient during a scan, relaxation of one or more muscles (e.g., creep), coughing, etc. In current systems, non-periodic motion can result in unusable (or non-diagnostic) images due to motion blur or changes in location.

SUMMARY

In various embodiments, a method for automated motion correct of nuclear images is disclosed. The method includes receiving a first set of imaging data including a plurality if annihilation events detected during an imaging period and generating a plurality of four-dimensional volumetric images from the imaging data for the imaging period. Each four-dimensional volumetric image includes a target tissue. At least one motion correction is determined for each of the plurality of four-dimensional volumetric images. The at least one motion correction is determined using target tracking data generated for the target organ over a time period associated with the four-dimensional volumetric image. Corrected imaging data is generated from the first set of imaging data and the at least one motion correction and at least one static reconstruction image including the target tissue during the imaging period is generated from the corrected imaging data.

In various embodiments, a system is disclosed. The system includes a first imaging modality configured to generate a first set of imaging data including a plurality of annihilation events during a first imaging period and a computer configured to receive the first set of imaging data and generate a plurality of four-dimensional volumetric images from the imaging data for the imaging period. Each four-dimensional volumetric image includes a target organ. The computer is further configured to determine a motion vector offset for each of the plurality of four-dimensional volumetric images. The motion vector offsets are determined using target tracking data generated for the target organ over a time period associated with the four-dimensional volumetric image. The computer is configured to generate a corrected image data from the first set of imaging data and the motion vector offsets and generate at least one static reconstruction image including the target organ during the imaging period from the corrected imaging data.

In various embodiments, a non-transitory computer readable medium storing instructions is disclosed. The instruction are configured to cause a computer system to execute the steps of receiving a first set of imaging data including a plurality if annihilation events detected during an imaging period and generating a plurality of four-dimensional volumetric images from the imaging data for the imaging period. Each four-dimensional volumetric image includes a target organ. The instructions are further configured to cause the computer to execute a step of determining a motion vector offset for each of the plurality of four-dimensional volumetric images. The motion vector offsets are determined using target tracking data generated for the target organ over a time period associated with the four-dimensional volumetric image. The instructions are further configured to cause the computer to execute the steps of generating corrected imaging data from the first set of imaging data and the motion vector offsets and generating at least one static reconstruction image including the target organ during the imaging period from the corrected imaging data.

BRIEF DESCRIPTION OF THE DRAWINGS

The following will be apparent from elements of the figures, which are provided for illustrative purposes and are not necessarily drawn to scale.

DETAILED DESCRIPTION

This description of the exemplary embodiments is intended to be read in connection with the accompanying drawings, which are to be considered part of the entire written description.

Various embodiments of the present disclosure address the foregoing challenges associated with generating diagnostic PET images from data sets having non-periodic movement. In some embodiments, a plurality of four-dimensional volumetric images are generated from imaging data for a predetermined imaging period. Each four-dimensional volumetric image includes target tissue. A motion vector offset is determined for each of the plurality of four-dimensional volumetric images. The motion vector offsets are determined using target tracking data generated for the target tissue over a time period associated with the four-dimensional volumetric image. Corrected imaging data is generated from the first set of imaging data and the motion vector offsets and at least one static reconstruction image including the target tissue during the imaging period is generated from the corrected imaging data.

Figure 1:
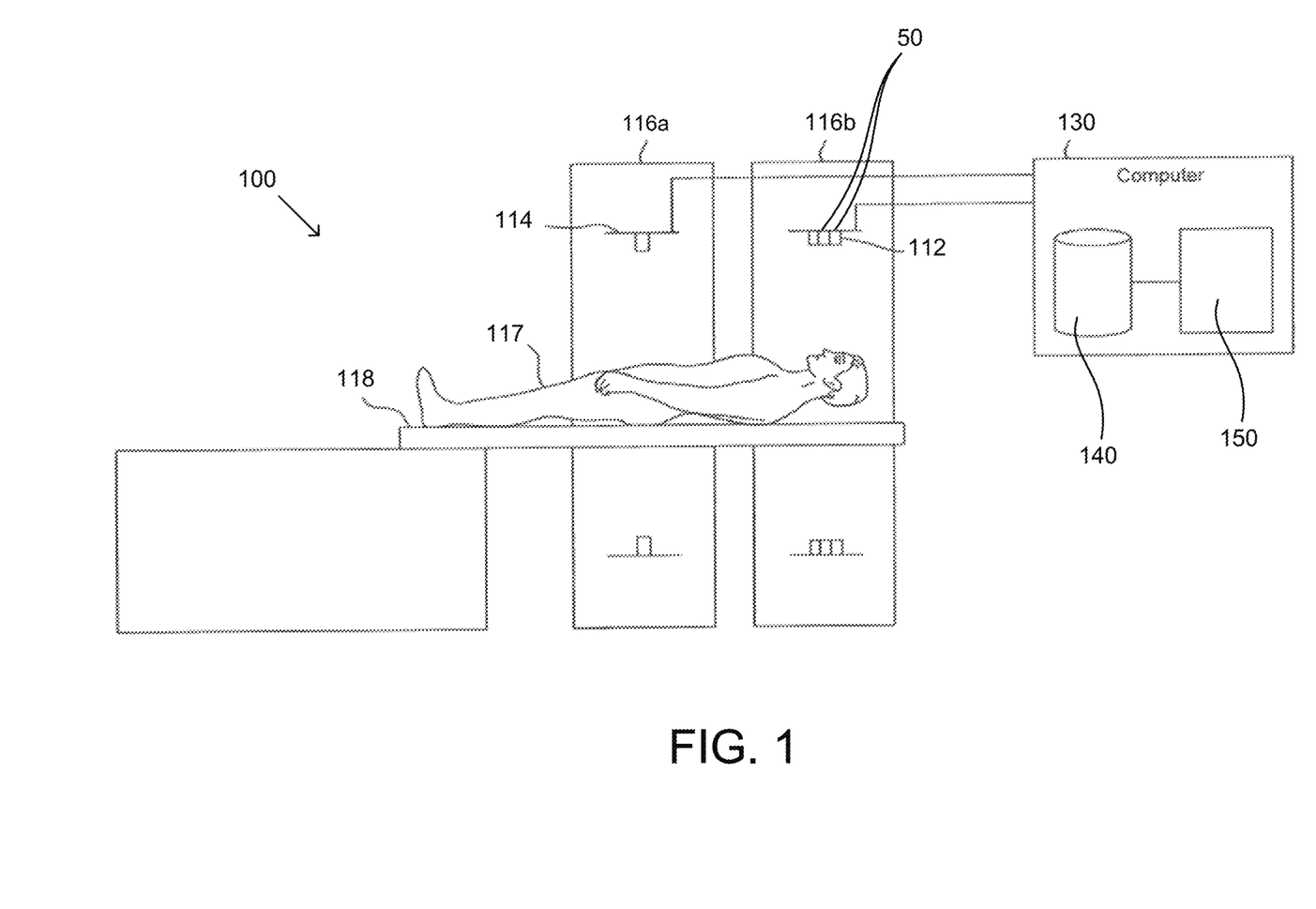
FIG. 1 illustrates a PET imaging system, in accordance with some embodiments.

FIG. 1 illustrates one embodiment of a nuclear imaging detector 100. The nuclear imaging detector 100 includes a scanner for at least a first modality 112 provided in a first gantry 116a. The first modality 112 includes a plurality of detectors 50 configured to detect an annihilation photon, gamma ray, and/or other nuclear imaging event. In various embodiments, the first modality 112 is a PET detector. A patient 117 lies on a movable patient bed 118 that may be movable between a gantry. In some embodiments, the nuclear imaging detector 100 includes a scanner for a second imaging modality 114 provided in a second gantry 116b. The second imaging modality 114 can be any suitable imaging modality, such as, for example, computerized tomography (CT), single-photon emission tomography (SPECT) and/or any other suitable imaging modality.

Scan data from the first modality 112 is stored at one or more computer databases 140 and processed by one or more computer processors 150 of a computer 130. The graphical depiction of computer 130 in FIG. 1 is provided by way of illustration only, and computer 130 may include one or more separate computing devices. The imaging data sets can be provided by the first modality 112 and/or may be provided as a separate data set, such as, for example, from a memory coupled to the computer 130. The computer 130 can include one or more processing electronics for processing a signal received from one of the plurality of detectors 50.

Figure 2A:
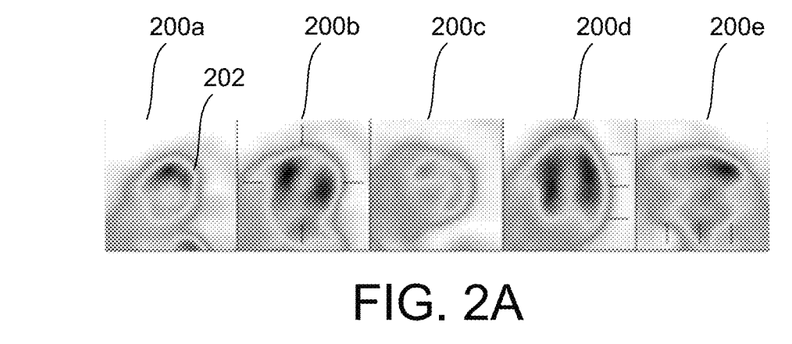
FIG. 2A illustrates a plurality of static images of an organ including non-periodic motion, in accordance with some embodiments.
Figure 2B:
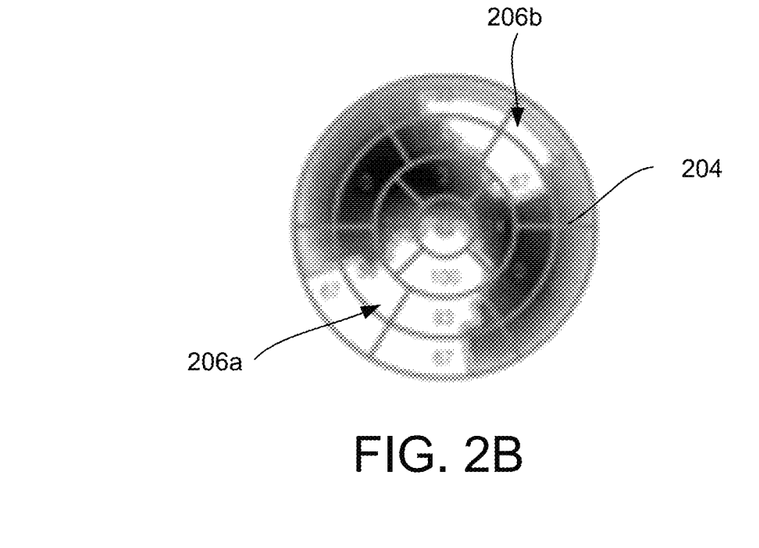
FIG. 2B illustrates a polar image generated from the plurality of static images of FIG. 2A, in accordance with some embodiments.

FIG. 2A illustrates a plurality of static images 200a-200e of a target organ 202, such as a heart. The plurality of static images 200a-200e are generated for a predetermined imaging period, for example, using the nuclear imaging detector 100. During the PET imaging procedure, movement, discomfort, and/or physiological reactions of the patient can result in non-periodic movement within the data. When non-periodic movement is present, significant artefacts and/or motion blur can occur. For example, the plurality of static images 200a-200e include significant motion blur caused by the non-periodic motion of the patient during imaging. As shown in FIG. 2B, a polar image 204 of the target organ 202 generated from the plurality of static images 200a-200e also includes significant artefacts 206a-206b as a result of the non-periodic motion. The non-periodic motion results in static images 200a-200e and a polar image 204 of a non-diagnostic quality, i.e., the images 200a-200e, 204 cannot be used for diagnosing defects or other issues in the target organ 202, resulting in the need to do additional diagnostic imaging of the patient and exposing the patient to additional radiation and discomfort.

Figure 3:
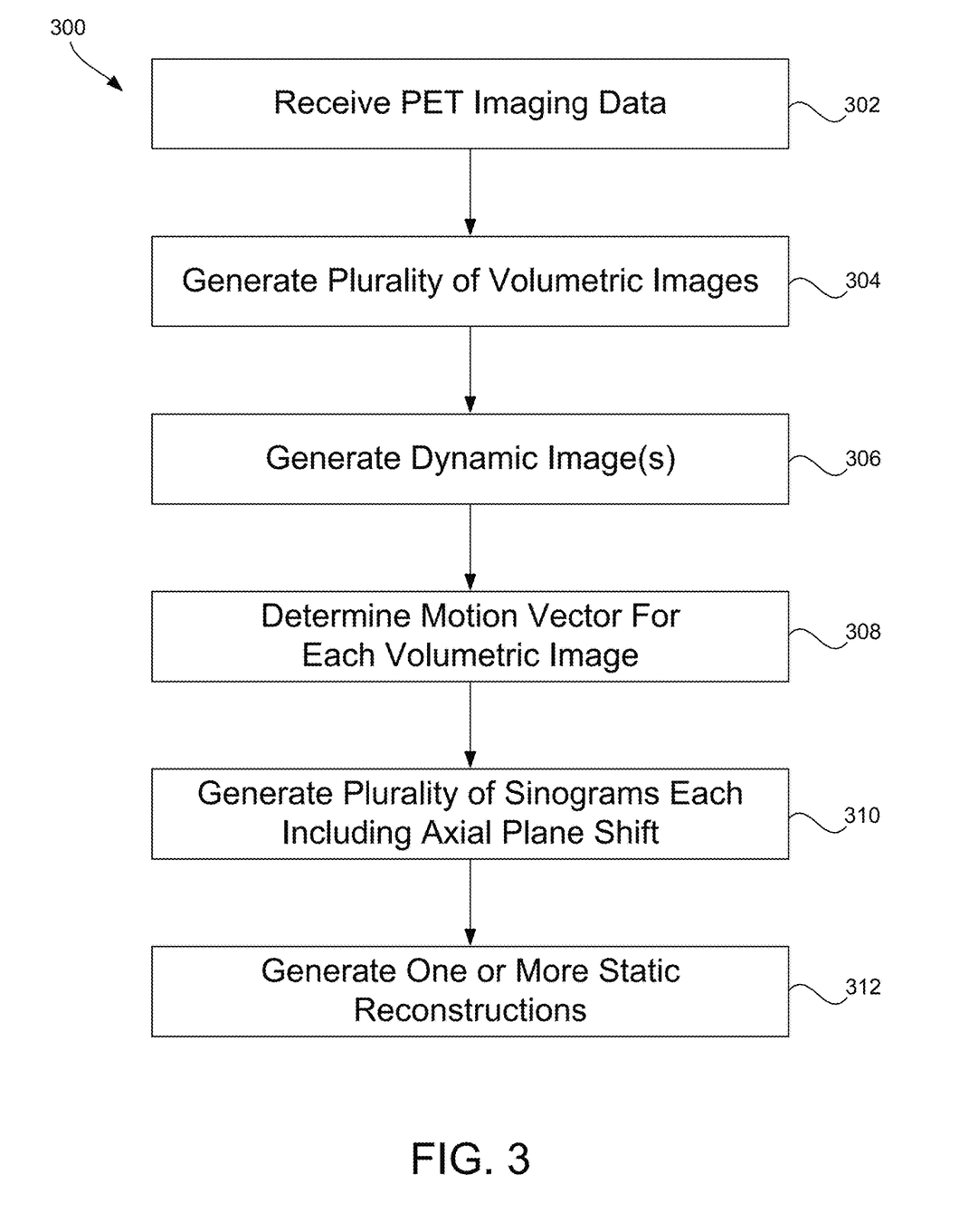
FIG. 3 illustrates a method of motion correction for static images in a PET scanning system, in accordance with some embodiments.

In some embodiments, systems and methods of motion correction are applied to PET imaging data to correct motion blue and/or artefacts introduced by non-periodic movement. FIG. 3 is a flowchart 300 illustrating a method of non-periodic motion correction for PET images, in accordance with some embodiments. The method 300 is configured to identify and track the position of a target organ 204, such as a heart, during reconstruction of diagnostic images to allow removal and/or minimization of non-periodic movement and related artefacts. The method 300 allow generations of diagnostic images from image data that traditionally produces non-diagnostic images, such as, for example, the PET image data associated with the static images 200a-200e in FIG. 2A.

At step 302, PET imaging data is received by a system, such as, for example, the computer 130. The imaging data can include PET image data for each detection event detected by an imaging modality, such as the first modality 112, during a nuclear imaging procedure. In some embodiments, the imaging data is generated and provided to the system in real-time (e.g., immediately provided from the imaging modality to the system). In other embodiments, the imaging data is generated by the imaging modality during an imaging period and is processed by the system during a later image generation period. In some embodiments, the image data is provided in a listmode format, although it will be appreciated that the data can be provided in any format readable by the system and converted into a listmode format.

Figure 4:
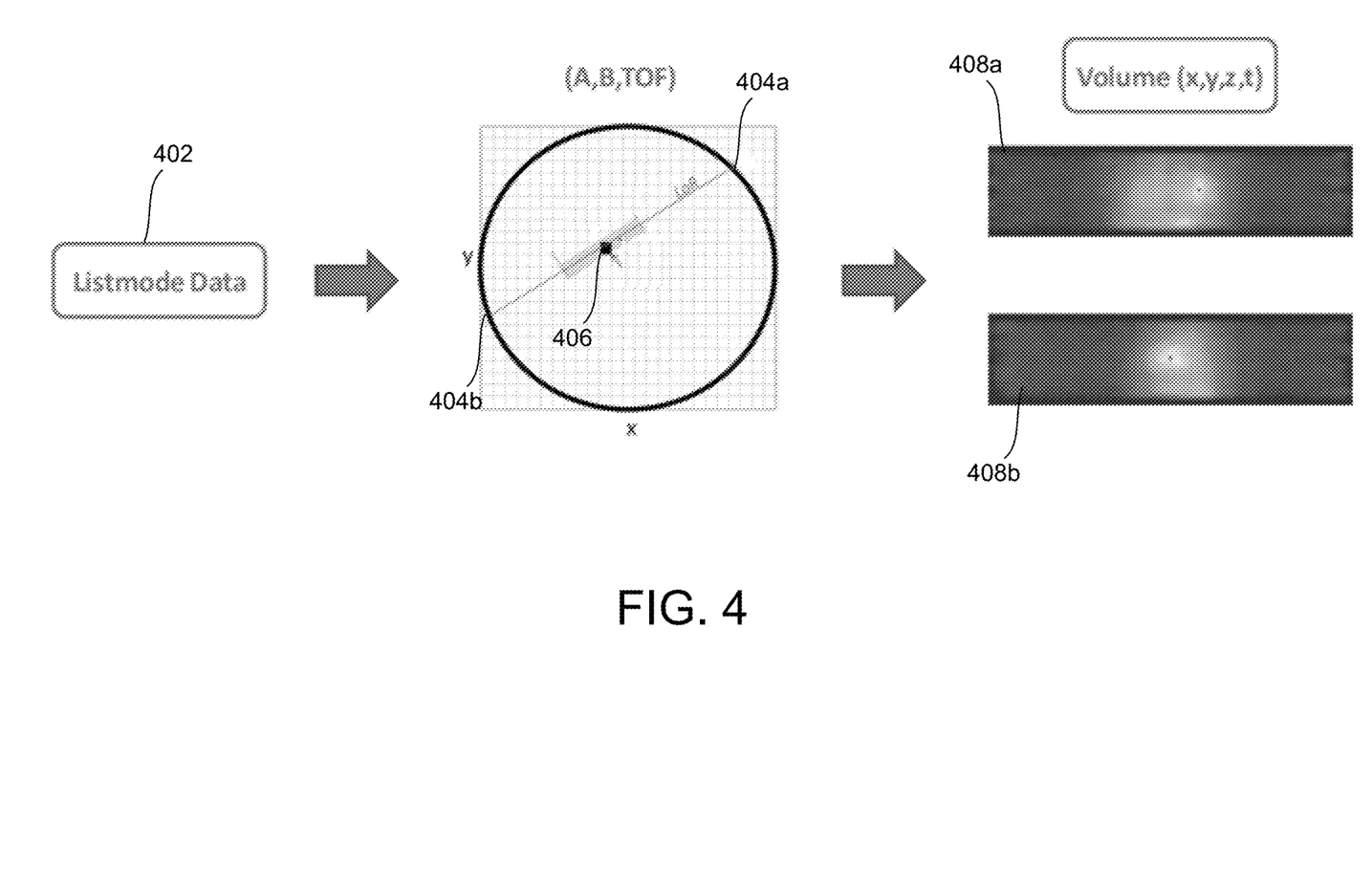
FIG. 4 illustrates a process flow of generating a plurality of four-dimensional volumetric images, in accordance with some embodiments.

At step 304, a plurality of volumetric images are generated directly from the listmode data 402. For example, as illustrated in FIG. 4, the listmode data 402 includes a plurality of data points each including a first detector identifier (A), a second detector identifier (B), and time-of-flight (TOF), i.e., $\{(A_1, B_1, TOF_1); (A_2, B_2, TOF_2) \ldots (A_n, B_n, TOF_n)\}$. The first detector identifier (A) and the second detector identifier (B) correspond to detectors 404a, 404b that each detect an annihilation event. Using the detector identifiers and the time-of-flight, the system (such as computer 130) identifies a position 406, or voxel, for the annihilation event. The system generates static volumetric images including each annihilation event in the listmode data 402 over a predetermined diagnostic period, e.g., a four-dimensional volumetric images 408a, 408b (or frames). Each four-dimensional volumetric image 408a, 408b includes three spatial dimensions (x, y, z) and a temporal dimension (t) corresponding to the predetermined time period selected from the predetermined diagnostic period.

In some embodiments, the temporal dimension t includes 1 second incremental intervals, although it will be appreciated that shorter and/or longer temporal dimensions can be selected. For example, in some embodiments, a first four-dimensional volumetric image is generated for a first time period (e.g., 0-1 second), a second four-dimensional volumetric image is generated for a second time period (e.g., 1-2 seconds), and an nth four-dimensional volumetric image is generated for an nth time period (e.g., (n−1)−n seconds). In some embodiments, the total number of volumetric images generated is equal to the total imagine period ($t_{total}$) divided by the temporal dimension increment t, e.g., 1 second, 2 seconds, 0.5 seconds, etc. The predetermined diagnostic period can include an entire imaging procedure and/or a portion of an imaging procedure excluding non-diagnostic imaging such as an ingestion and/or diffusion period prior to a tracer being distributed to target tissue.

At step 306, a dynamic image of the target tissue is generated for the predetermined diagnostic period. A single continuous dynamic image is generated for the entire predetermined diagnostic period and/or a plurality of dynamic images for portions of the predetermined diagnostic period can be generated. In some embodiments, the dynamic image is generated using imaging data generated by a second imaging modality 114, such as a CT imaging modality. The second set of imaging data is generated simultaneously with the set of PET imaging data. The position of a target tissue is identified within the dynamic image using one or more known target identification processes. For example, in various embodiments, the identification of the target tissue can include, but is not limited to, organ finding using a matched filter for acquisition and normalized cross-correlation for tracking. In some embodiments, a center of the target tissue is identified within the dynamic image.

Figure 5:
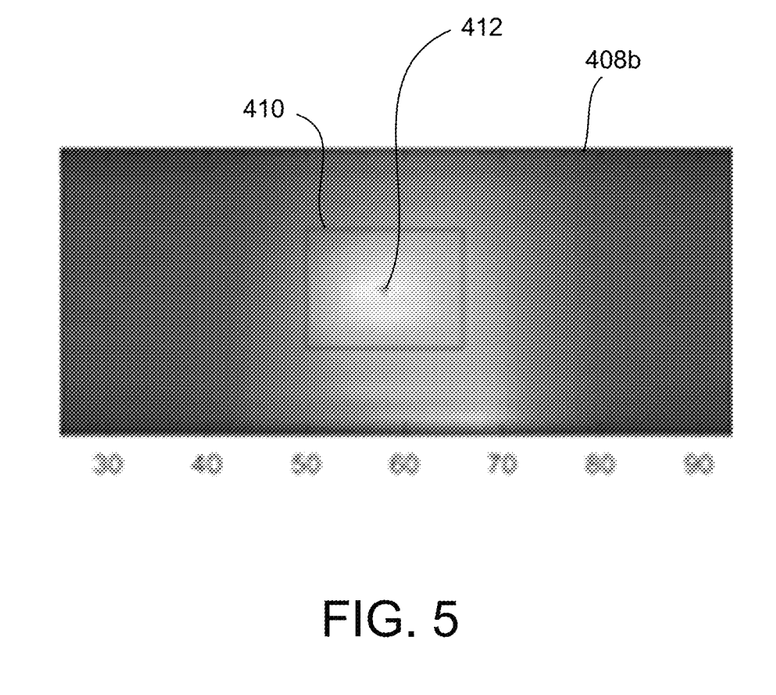
FIG. 5 illustrates target acquisition in a four-dimensional volumetric image of target tissue identified using a target acquisition process, in accordance with some embodiments.

At step 308, a motion vector is generated for each four-dimensional volumetric image 408a, 408b using target tracking data generated from the dynamic image (or portion of the dynamic image) corresponding to the temporal dimension t of the selected four-dimensional volumetric image 408a, 408b. For example, in some embodiments, motion and position information from the dynamic image is used to identify the target tissue 410 and/or a center point 412 of the target tissue 410 within each four-dimensional volumetric image 408b, as shown in FIG. 5. Although embodiments are illustrated and discussed including translational tracking of target tissue 410, it will be appreciated that any type of movement, such as translational, rotational, skew, non-rigid transformations, etc. may be tracked and used to generate a motion vector.

Figure 6:
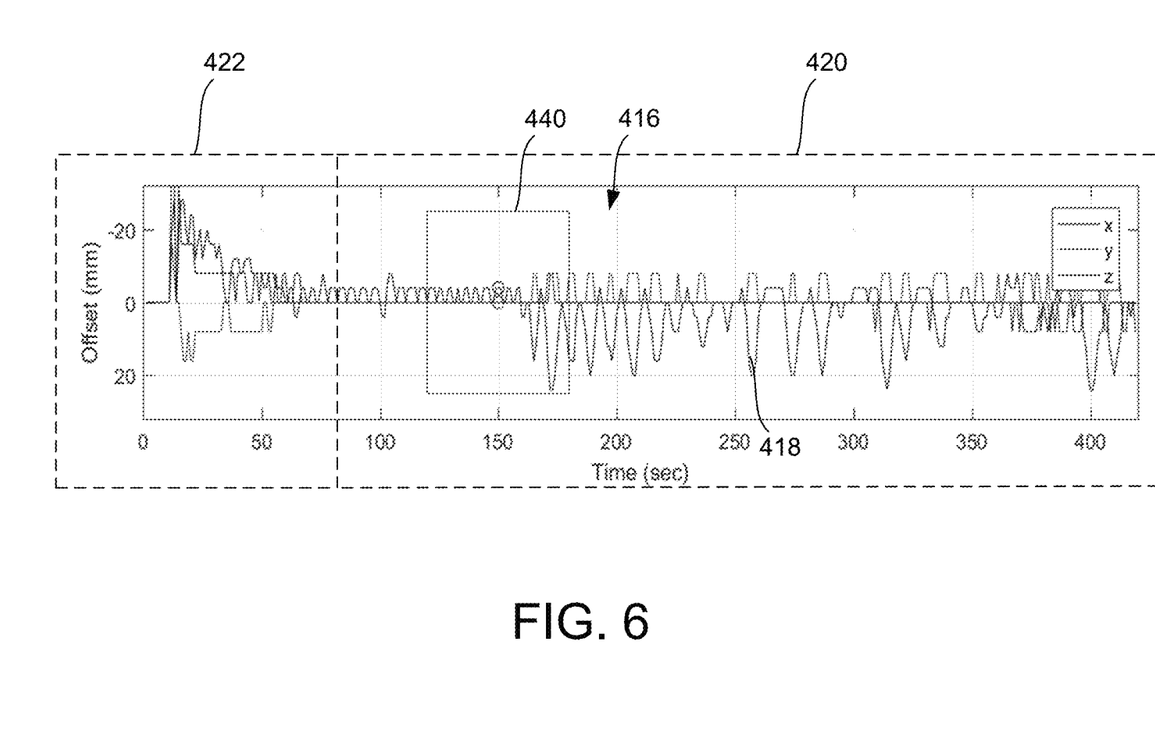
FIG. 6 is a chart illustrating motion vector offsets determined using target tracking of a target organ within a plurality of four-dimensional volumetric images, in accordance with some embodiments.

Motion and position information generated from the dynamic image is referenced to each image in the plurality of volumetric images to generate a set of motion vectors for the selected diagnostic period within the listmode data set 402. FIG. 6 is a chart 416 illustrating motion vector offsets 418 for the listmode data 402. The greater the offset 418, the greater the non-periodic movement of the target tissue 410 during the temporal period t of the corresponding four-dimensional volumetric image 408b. In some embodiments, a non-diagnostic portion 422 of the listmode data 402 corresponding to ingestion and diffusion of a tracer molecule is ignored (e.g., not used for diagnostic imaging), although it will be appreciated that additional target tracking and/or diagnostic procedures may be performed that include the ingestion and/or diffusion periods. For example, during early phases of a cardiac scan, the signature of a target organ (i.e., target tissue) changes. In some embodiments, motion tracking through the changes in the target tissue can be tracked and motion correction applied according to the embodiments disclosed herein.

Figure 7:
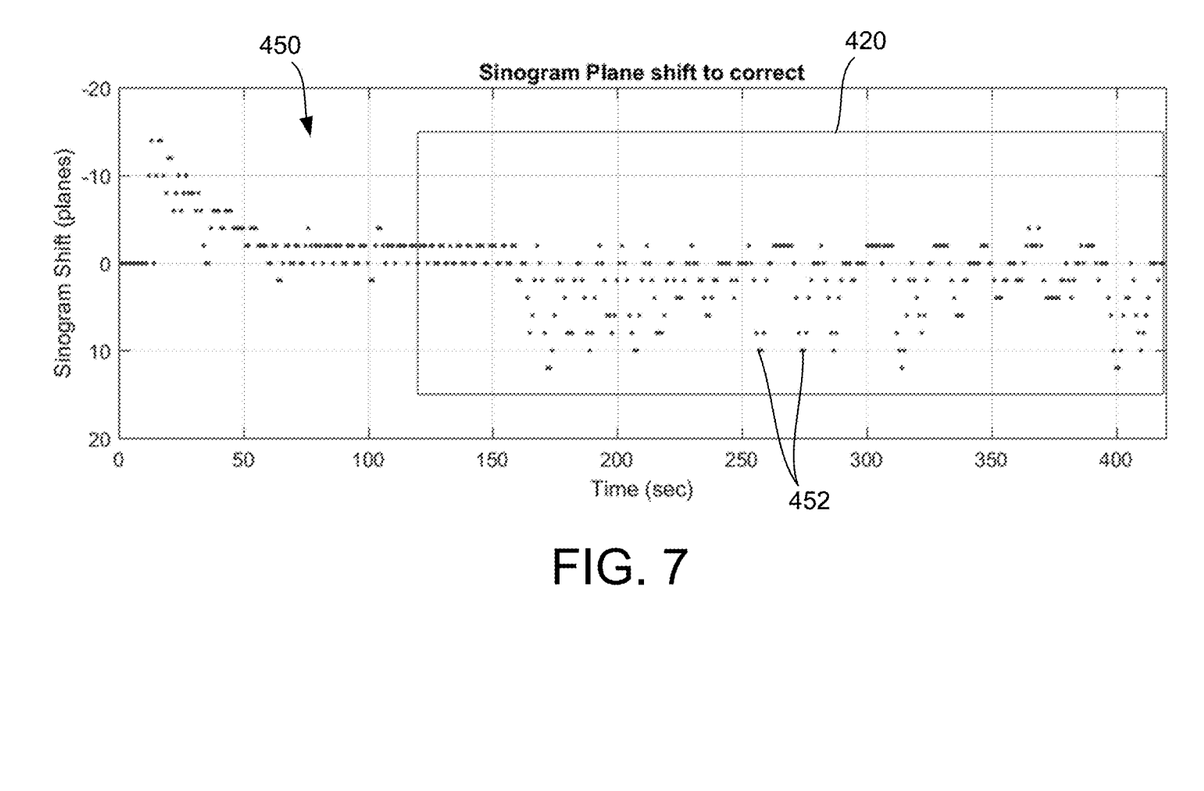
FIG. 7 is a chart illustrating a plurality of sinogram plane shift correction values applied to image data during generation of corrected imaging data, in accordance with some embodiments.

At step 310, corrected data including axial plane shifts (or other motion correction shifts) corresponding to the motion vector offsets 418 is generated for the listmode data 402. In some embodiments, the plane shifts correspond to discrete shift values on a predetermined axis, such as a z-axis. FIG. 7 is a chart 450 illustrating a plurality of discrete shifts 452 applied to the listmode data 402 during generation of corrected data from the listmode data 402. For example, in some embodiments, a discrete shift value is applied to one or more voxels within the temporal period t to correct a position of the voxel during grouping and reconstruction. In some embodiments, the corrected data is generated using only a predetermined diagnostic portion 420 of the imaging period. In some embodiments, pre-processing of the listmode data 402 can be applied prior to generation of the corrected imaging data, such as, for example, correction for random coincidences, estimation and subtraction of scattered photons, detector dead-time correction, and/or detector-sensitivity correction.

At step 312, one or more reconstructed static images are generated from the corrected imaging data. The reconstruction can be generated according to known methods for generating PET diagnostic images from the corrected imaging data, such as, for example, filtered back projection, statistical-likelihood based-approaches (e.g., Shepp-Vargi construction), Bayesian constructions, and/or any other suitable method of generating static PET reconstruction images from the corrected imaging data.

Figure 8A:
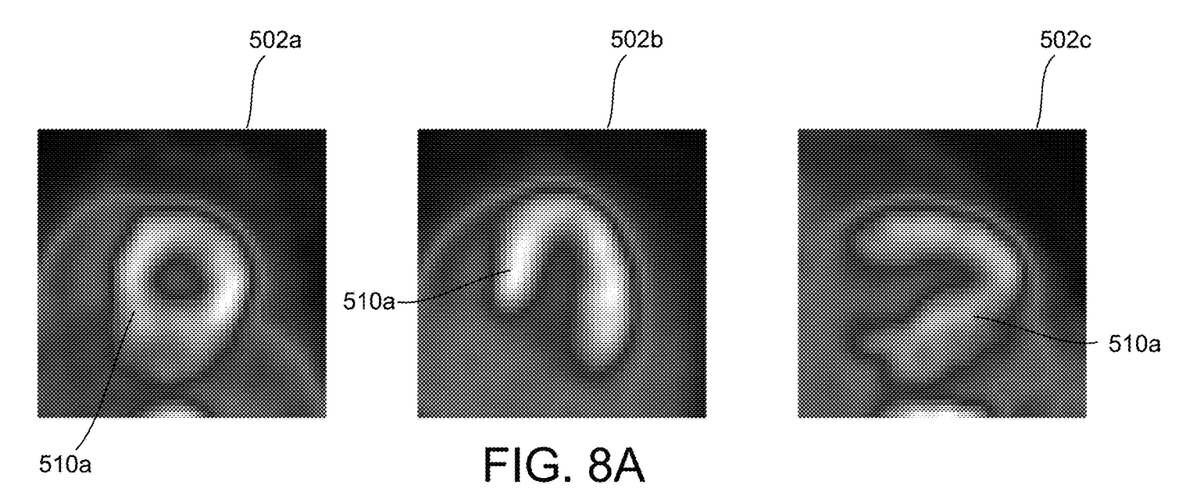
FIG. 8A illustrates a plurality of reconstructed static images generated from imaging data collected during the imaging period illustrated in FIG. 6 using a traditional reconstruction process.
Figure 8B:
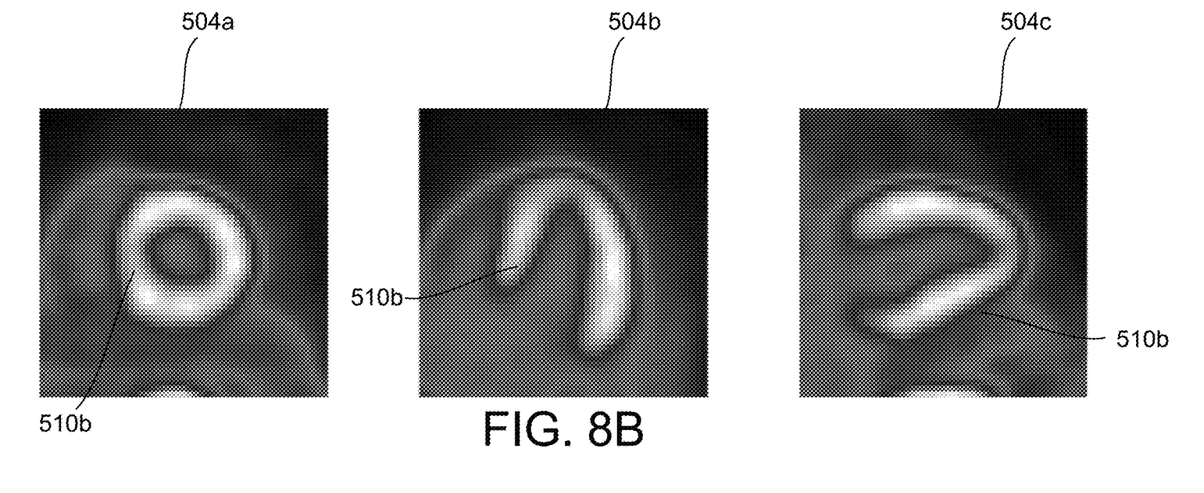
FIG. 8B illustrates a plurality of reconstructed static images generated from the imaging data collected during the imaging period illustrated in FIG. 6, in accordance with some embodiments.

In some embodiments, the method 300 results in the removal of artefacts, such as artefacts 206a-206b illustrated in FIG. 2B, and allows generation of diagnostic-quality reconstructed images from traditionally non-diagnostic listmode data 402. For example, the listmode data 402 includes significant non-periodic motion, such as, for example, as highlighted by box 440 in FIG. 6. FIG. 8A illustrates a plurality of static images 502a-502c of the target tissue 510a generated from the listmode data 402 using traditional methods. As shown in FIG. 8A, the static images 502a-502c have significant motion blur and artefacts such that the images are of non-diagnostic quality and cannot be used for patient diagnosis. FIG. 8B illustrates reconstructions of the target tissue 510b generated from the listmode data 402 using the method 100 of motion correction discussed in conjunction with FIGS. 3-7. As can be seen in FIG. 8B, the motion blur and artefacts of each static image 504a-504c has been eliminated and/or minimized as compared to the static images 502a-502c generated using a non-motion corrected data. The motion corrected static images 504a-504c are of diagnostic quality and can be used in patient diagnosis.

Figure 9A:
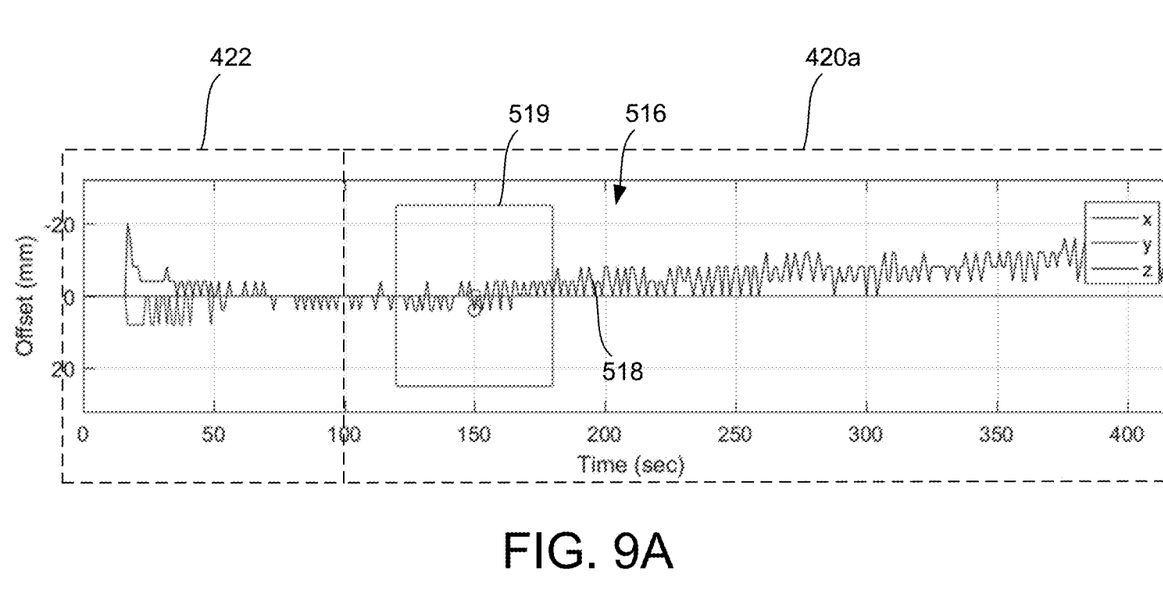
FIG. 9A is a chart illustrating an imaging procedure having an imaging period including non-periodic movement of an organ, in accordance with some embodiments.
Figure 9B:
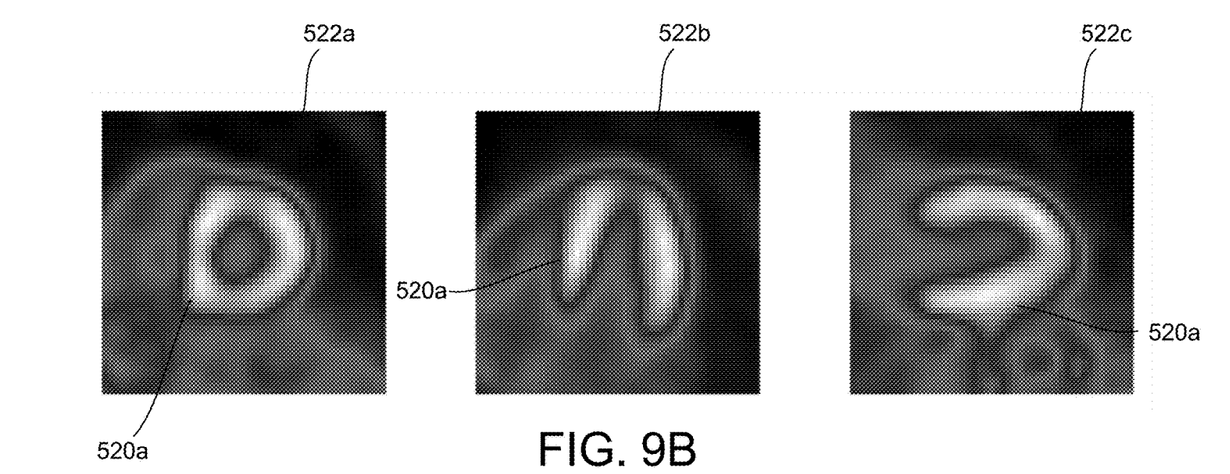
FIG. 9B a plurality of reconstructed static images generated from imaging data collected during the imaging period illustrated in FIG. 9A using a traditional reconstruction process.
Figure 9C:
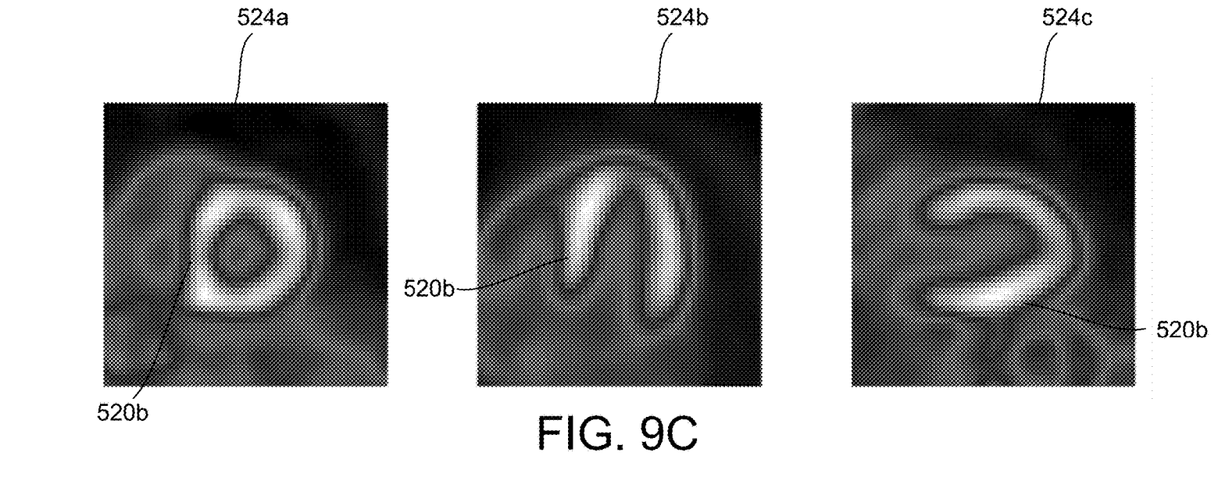
FIG. 9C illustrates a plurality of reconstructed static images generated from the imaging data collected during the imaging period illustrated in FIG. 9A, in accordance with some embodiments.

Similarly, FIG. 9A is a chart 516 illustrating motion vector offsets 518 for listmode PET data including non-periodic organ creep or movement during a diagnostic period 420a, for example, as highlighted by box 519. Organ creep occurs due to relaxation of one or more muscles during an imaging period. As the one or more muscles relax, the position of the organ within the patient shifts. This movement is non-periodic and results in distortion of a reconstructed image due to the change in position of the organ during imaging. FIG. 9B illustrates a plurality of static images 522a-522c of target tissue 520a generated by a traditional reconstruction from the listmode data associated with FIG. 9A using traditional methods. As shown in FIG. 9B, the traditional reconstruction produces static images having artefacts due to organ creep of the target tissue 520a. Although the images are of diagnostic quality, artefacts in the images 522a-522c can result in incorrect or missed diagnosis. FIG. 9C illustrates a plurality of static images 524a-524c of the target tissue 520b generated from the listmode PET data of chart 516 according to the methods disclosed herein. As shown in FIG. 9C, the artefacts of the traditional static images 522a-522c are removed, the edges of the target tissue 520b are more defined, and the diagnostic quality of the images 524a-524c is increased over a traditional static image 522a-522c.

Figure 10A:
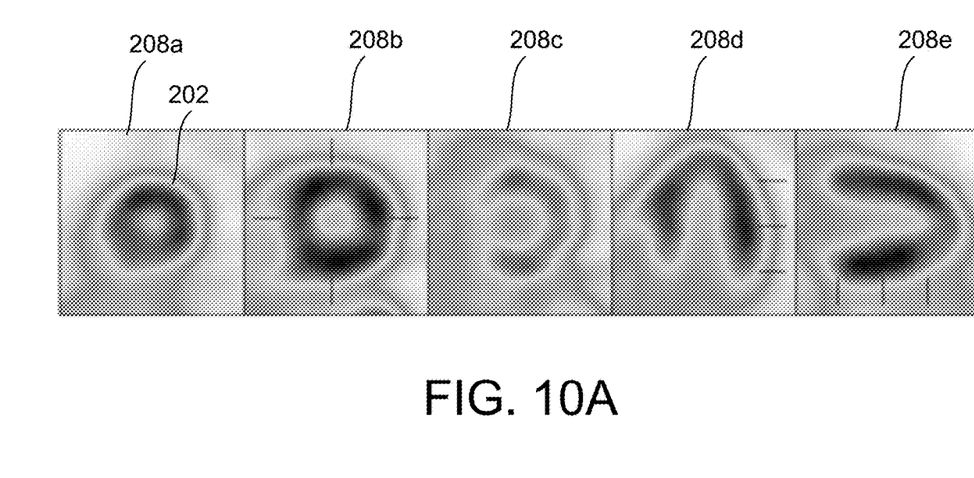
FIG. 10A illustrates a plurality of static images of an organ generated using a method of motion correction, in accordance with some embodiments.
Figure 10B:
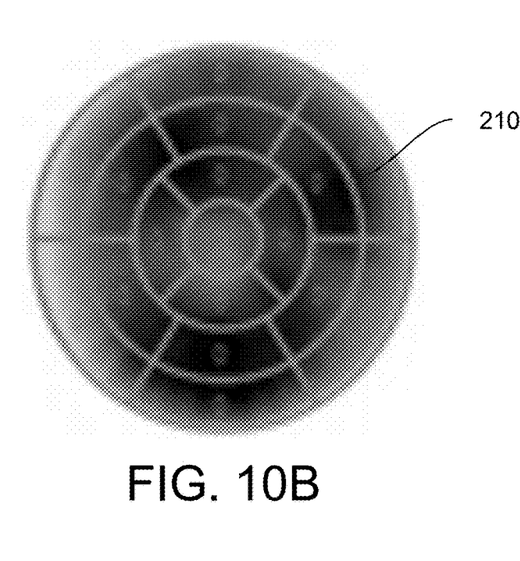
FIG. 10B illustrates a polar image generated from the plurality of static images of FIG. 10A, in accordance with some embodiments.

FIGS. 10A and 10B illustrate the scan data of FIGS. 2A and 2B, respectively, after undergoing a motion correction method as disclosed herein. As shown in FIG. 10B, the polar image 210 generated from the plurality of motion corrected static images 208a-208e does not contain any of the defects 206a-206b included in the original polar image 204. By applying the methods and systems disclosed herein, a diagnostic images 208a-208e, 210 can be generated from data that traditionally generated only non-diagnostic images.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A computer-implemented method, comprising:
receiving a first set of imaging data including a plurality of annihilation events detected by a first imaging modality during an imaging period;
generating a plurality of four-dimensional volumetric images from the first set of imaging data, wherein each of the plurality of four-dimensional volumetric images is a static image including a target tissue, and wherein each of the plurality of four-dimensional volumetric images has a predetermined temporal dimension;
generating at least one dynamic image including movement of the target tissue during a predetermined temporal period including at least a portion of the imaging period;
determining at least one motion correction for each of the plurality of four-dimensional volumetric images, wherein the at least one motion correction comprises a motion vector generated for a corresponding one of the plurality of four-dimensional volumetric images using target tracking data generated for the target tissue from the dynamic image over a portion of the predetermined temporal period corresponding to the predetermined temporal dimension of the corresponding one of the plurality of four-dimensional volumetric images;
generating corrected image data from the first set of imaging data and the at least one motion correction by:
determining at least one axial plane shift value for each of the plurality of four-dimensional volumetric images, wherein the axial plane shift value is generated from the dynamic image;
shifting a subset of the first set of imaging data by the at least one axial plane shift value; and
generating a sinogram from the shifted subset; and
generating at least one static reconstruction image including the target tissue during the imaging period from the corrected image data.

2. The computer-implemented method of claim 1, wherein determining the at least one motion correction for each of the plurality of four-dimensional volumetric images comprises:
identifying a location of the target tissue within the dynamic image;
identifying a position of the target tissue within the corresponding one of the plurality of four-dimensional volumetric images based on the location of the target organ within the dynamic image during the portion of the predetermined temporal period corresponding to the predetermined temporal dimension of the corresponding one of the plurality of four-dimensional volumetric images; and
generating the motion vector for the corresponding one of the plurality of four-dimensional volumetric images based on movement of the target tissue within the dynamic image during the portion of the predetermined temporal period corresponding to the predetermined temporal dimension of the corresponding one of the plurality of four-dimensional volumetric images.

3. The computer-implemented method of claim 2, wherein the location of the target tissue within the dynamic image is identified using target tracking of the target tissue.

4. The computer-implemented method of claim 2, wherein the at least one dynamic image is generated from a set of imaging data generated during at least a portion of the imaging period.

5. The computer-implemented method of claim 4, wherein the second set of imaging data is generated by a second imaging modality.

6. The computer-implemented method of claim 1, wherein the first set of imaging data comprises a PET listmode data set.

7. The computer-implemented method of claim 1, wherein the predetermined temporal dimension associated with each of the plurality of four-dimensional volumetric images is 1 second.

8. The computer-implemented method of claim 1, wherein the target tissue is an organ.

9. A system, comprising:
a first imaging modality configured to generate a first set of imaging data including a plurality of annihilation events during a first imaging period; and
a computer, wherein the computer is configured to:
receive the first set of imaging data;
generate a plurality of four-dimensional volumetric images from the first set of imaging data, wherein each of the plurality of four-dimensional volumetric images is a static image including a target tissue, and wherein each of the plurality of four-dimensional volumetric images has a predetermined temporal dimension;
generate at least one dynamic image including movement of the target tissue during a predetermined temporal period;
determine at least one motion correction for each of the plurality of four-dimensional volumetric images, wherein the at least one motion correction comprises a motion vector generated for a corresponding one of the plurality of four-dimensional volumetric images using target tracking data generated for the target tissue from the dynamic image over a portion of the predetermined temporal period corresponding to the predetermined temporal dimension of the corresponding one of the plurality of four-dimensional volumetric images;

generate corrected image data from the first set of imaging data and the motion vector offsets by:
determining at least one axial plane shift value for each of the plurality of four-dimensional volumetric images, wherein the axial plane shift value is generated from the motion vector offsets;
shift a subset of the first set of imaging data by the axial plane shift value; and
generate a sinogram from the shifted subset; and generate at least one static reconstruction image including the target tissue during the imaging period from the corrected image data.

10. The system of claim 9, wherein the computer is configured to:
identify a location of the target tissue within the dynamic image;
identify a position of the target tissue within the corresponding one of the plurality of four-dimensional volumetric images based on the location of the target organ within the dynamic image during the portion of the predetermined temporal period corresponding to the predetermined temporal dimension of the corresponding one of the plurality of four-dimensional volumetric images; and
generate the motion vector for the corresponding one of the plurality of four-dimensional volumetric images based on movement of the target tissue within the dynamic image during the portion of the predetermined temporal period corresponding to the predetermined temporal dimension of the corresponding one of the plurality of four-dimensional volumetric images.

11. The system of claim 10, wherein the location of the target tissue within the dynamic image is identified using target tracking of the target tissue.

12. The system of claim 10, comprising a second imaging modality configured to generate a second set of imaging data during a second imaging period, wherein the at least one dynamic image is generated from the second set of imaging data.

13. The system of claim 9, wherein the first imaging modality is a positron emission tomography (PET) imaging modality.

14. The system of claim 9, wherein the computer is configured to convert the first set of imaging data to listmode data.

15. The system of claim 9, wherein the predetermined temporal dimension associated with each of the plurality of four-dimensional volumetric images is 1 second.

16. A non-transitory computer readable medium storing instructions configured to cause a processor to execute the steps of:

receiving a first set of imaging data including a plurality of annihilation events detected by a first imaging modality during an imaging period;
generating a plurality of four-dimensional volumetric images from the imaging data for the imaging period, wherein each of the plurality of four-dimensional volumetric images is a static image including a target tissue, and wherein each of the plurality of four-dimensional volumetric images has a predetermined temporal dimension;
generating at least one dynamic image including movement of the target tissue during a predetermined temporal period;
determining at least one motion correction for each of the plurality of four-dimensional volumetric images, wherein the at least one motion correction comprises a motion vector generated for a corresponding one of the plurality of four-dimensional volumetric images using target tracking data generated for the target tissue from the dynamic image over a portion of the predetermined temporal period corresponding to the predetermined temporal dimension of the corresponding one of the plurality of four-dimensional volumetric images;
generating corrected image data from the first set of imaging data and the at least one motion correction by:
determining at least one axial plane shift value for each of the plurality of four-dimensional volumetric images, wherein the axial plane shift value is generated from the dynamic image;
shifting a subset of the first set of imaging data by the at least one axial plane shift value; and
generating a sinogram from the shifted subset; and
generating at least one static reconstruction image including the target tissue during the imaging period from the corrected image data.

17. The non-transitory computer readable medium of claim 16, wherein the processor is configured to execute the steps of:
identifying a location of the target tissue within the dynamic image;
identifying a position of the target tissue within the corresponding one of the plurality of four-dimensional volumetric images based on the location of the target tissue within the dynamic image during the portion of the predetermined temporal period corresponding to the predetermined temporal dimension of the corresponding one of the plurality of four-dimensional volumetric images; and
generating the motion vector for the corresponding one of the plurality of four-dimensional volumetric images based on movement of the target tissue within the dynamic image during the portion of the predetermined temporal period corresponding to the predetermined temporal dimension of the corresponding one of the plurality of four-dimensional volumetric images.

* * * * *